US006800053B2

(12) United States Patent
Fox

(10) Patent No.: US 6,800,053 B2
(45) Date of Patent: Oct. 5, 2004

(54) METHOD AND APPARATUS FOR STERILIZING INTERNAL PASSAGES OF A CENTRIFUGE CENTRATE GATE

(75) Inventor: Mark J. Fox, Naugatuck, CT (US)

(73) Assignee: Kendro Laboratory Products, LP, Newtown, CT (US)

( * ) Notice: Subject to any disclaimer, the term of this patent is extended or adjusted under 35 U.S.C. 154(b) by 0 days.

(21) Appl. No.: 10/736,558

(22) Filed: Dec. 17, 2003

(65) Prior Publication Data

US 2004/0157718 A1 Aug. 12, 2004

Related U.S. Application Data

(60) Provisional application No. 60/435,255, filed on Dec. 23, 2002.

(51) Int. Cl.[7] ................................................ B04B 15/06
(52) U.S. Cl. ................................ 494/1; 494/13; 494/25; 422/26

(58) Field of Search ........................... 494/1, 13, 25–26, 494/55, 58, 59; 210/178, 372–376; 422/26

(56) References Cited

U.S. PATENT DOCUMENTS

| 4,109,853 | A | * | 8/1978 | Ruegg | 494/36 |
|---|---|---|---|---|---|
| 5,328,441 | A | * | 7/1994 | Carr | 494/58 |
| 5,733,238 | A | * | 3/1998 | Carr | 494/58 |
| 5,743,840 | A | * | 4/1998 | Carr | 494/13 |
| 2002/0016243 | A1 | * | 2/2002 | Carr | 494/37 |

FOREIGN PATENT DOCUMENTS

| JP | 2-290267 | * 11/1990 |
|---|---|---|
| JP | 2000-42449 | * 2/2000 |

* cited by examiner

Primary Examiner—Charles E. Cooley
(74) Attorney, Agent, or Firm—Baker & Hostetler LLP

(57) ABSTRACT

Method and apparatus for sterilization of laboratory equipment, which are particularly suited for sterilization of internal passages of a centrifuge centrate gate assembly.

20 Claims, 3 Drawing Sheets

METHOD AND APPARATUS FOR STERILIZING INTERNAL PASSAGES OF A CENTRIFUGE CENTRATE GATE

PRIORITY CLAIM

This application claims priority to provisional U.S. patent application Ser. No. 60/435,255, filed Dec. 23, 2002, the disclosure of which is incorporated herein by reference.

FIELD OF THE INVENTION

The present invention relates generally to the sterilization of laboratory equipment. More particularly, the present invention relates to the sterilization of internal passages of a centrifuge centrate gate assembly.

BACKGROUND OF THE INVENTION

In normal centrifuge operation the centrifuge may possibly have contaminants carried into the internal piston cavities of the centrate gate assembly. Since the temperature is not monitored in this area, direct steam injection is needed to ensure complete steaming of the system.

A centrifuge body generally contains a centrate gate internally. This gate serves the purpose of isolating and discharging solids from the centrate discharge portion of the centrifuge. This prevents contamination and loss of any product.

Normally the centrate gate is raised and lowered using a 4-way directional control valve. However, these valves are not suitable for steam operation. The present invention addresses and corrects these shortcomings.

Many different types of centrifugal separators are known for separating heterogeneous mixtures according to "their specific gravities components". A heterogeneous mixture, which may also be referred to as feed material or liquid feed, is injected into a rotating bowl of the separator. The bowl rotates at high speeds and forces particles of the mixture to separate from the liquid centrate. As a result, a dense solids cake compresses tightly against the surface of the bowl and the liquid centrate forms radially inward from the solids cake.

The bowl may rotate at speeds sufficient to produce 20,000 g's so that the solids may be separated from the centrate. Typically, the liquid feed travels at a relatively slow speed before being introduced through feed holes to the rotating bowl where the liquid feed is instantaneously accelerated to the angular speed of the rotating bowl. However, introducing the liquid feed to the bowl at such high speeds creates shear forces that often destroy a large amount of the solid component of the liquid feed before separation.

While the solids accumulate along the wall of the bowl, the centrate is drained. Once it is determined that a desired amount of the solids has been accumulated, the separator is placed in a discharge mode. In one such discharge mode, a scraper blade extending the length of the rotating bowl is placed in a scraping position against the separator wall and the bowl is rotated at a low scraping speed. Then, the solids are scraped from the sides of the bowl and fall toward a solids collecting outlet. However, such scraping systems do not effectively remove wet or sticky solids which may have the consistency of peanut butter. In such instances, the sticky solids remain stuck on the separator wall and scraper blades or fall from the wall and then reattach to the blades before reaching the collecting outlet. As a result, the solids recovery yield is reduced and the remaining solids undesirably contaminate the separator.

In equipment where potentially infectious specimens are processed and stored, contamination of the interior surfaces of the equipment and of the contents kept there due to spills and breakage of the specimens is an unfortunate but all too frequent occurrence. Removing the contaminated equipment from a busy laboratory for sterilization is often out of the question. Occasional manual cleaning with surface disinfectants has heretofore been the only practical solution. Another, less practical method of disinfecting, at least for smaller equipment, is to immerse it in glutaraldehyde. In some instances, contamination is so extensive that the equipment is discarded entirely and new equipment purchased to replace it.

Complete, in place sterilization of some laboratory equipment has not been possible, particularly in those items of equipment such as cold centrifuges and refrigerators having very cold interior surfaces or two or more zones of surfaces having widely differing temperatures. For example, some centrifuges maintain specimens at temperatures below 10° C. Other areas within the same centrifuge may be at room temperature.

In the centrifuge, airborne contamination is common. It would be desirable to sterilize the interior of the equipment before having to open it to remove the contents to spare the technician the risk of exposure to contamination. It would also be desirable to sterilize without the need of disassembly of the centrifuge.

It is an object of the present invention to provide an apparatus for sterilizing surfaces within equipment without having to disassemble the equipment, thereby decreasing costs and saving time. It is a further object of the present invention, to provide a process where surfaces can be sterilized by way of a novel valve assembly.

SUMMARY OF THE INVENTION

It is therefore a feature and advantage of the present invention to provide an apparatus and method for sterilizing the internal passages or cavities of a centrifuge centrate gate without the need to disassemble the centrifuge.

The above and other features and advantages are achieved through the use of a novel valve assembly as herein disclosed. In accordance with one aspect of the present invention there is provided a method of sterilizing a centrifuge, comprising the steps of lowering a centrate gate; closing an air control valve in communication with a gate cylinder; opening a first control valve, a second control valve, a third control valve and a fourth control valve which are all in communication with the gate cylinder; opening a steam control valve which is in communication with the gate cylinder thereby allowing steam to enter a piston cylinder cavity disposed within the gate cylinder; determining a system temperature; comparing the system temperature to a predetermined temperature; and toggling the centrate gate from a raised position to a lowered position until the predetermined temperature is reached.

In accordance with another aspect of the present invention there is provided an equipment sterilization apparatus, comprising means for lowering a centrate gate; means for closing an air control valve in communication with a gate cylinder; means for opening a first control valve, a second control valve, a third control valve and a fourth control valve which are all in communication with the gate cylinder; means for opening a steam control valve which is in communication with the gate cylinder thereby allowing steam to enter a piston cylinder cavity disposed within the gate cylinder; means for determining a system temperature;

means for comparing the system temperature to a predetermined temperature; and means for toggling the centrate gate from a raised position to a lowered position until the predetermined temperature is reached.

In accordance with yet another aspect of the present invention there is provided a centrifuge sterilization apparatus, comprising a controller; a centrate gate disposed within a centrifuge body; a valve assembly in communication with the centrate gate, an air supply and a steam supply; and a plurality of temperature elements in communication with the controller, wherein the controller is configured to operate the valve assembly.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DESCRIPTION OF THE INVENTION

Figure 1:
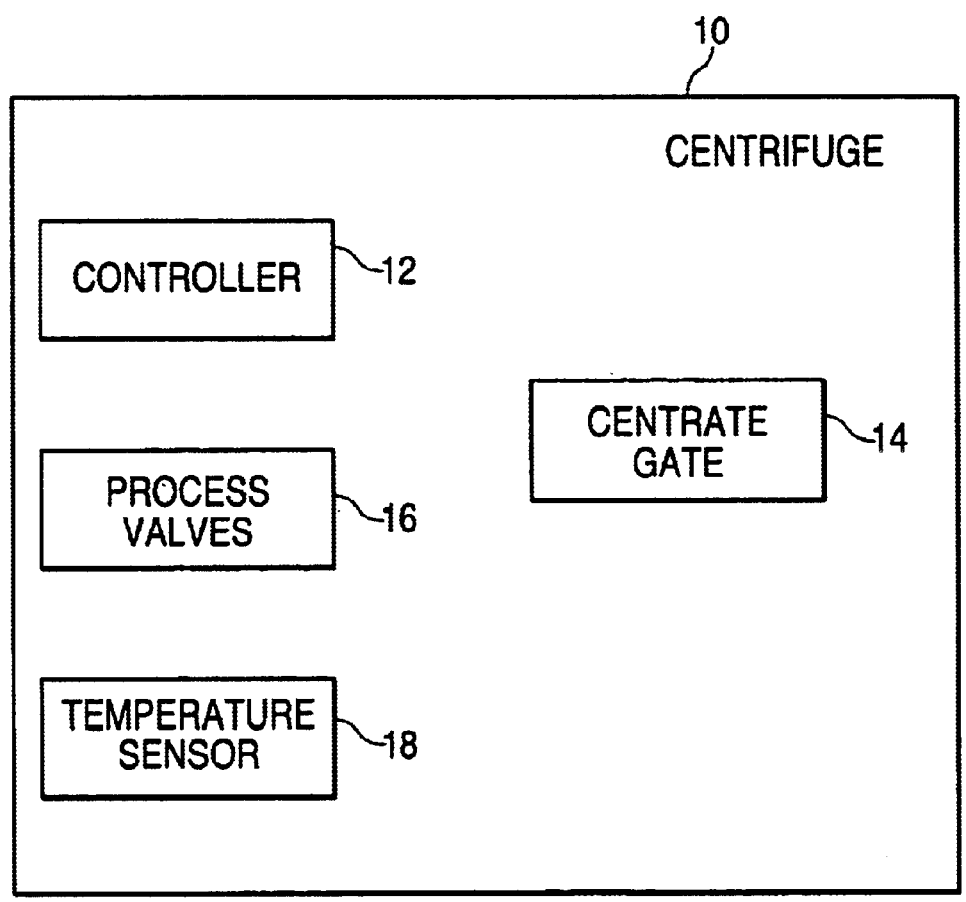
FIG. 1 is a block diagram of one preferred embodiment of the present invention.

The invention will now be described with reference to the drawing figures, in which like reference numerals refer to like parts throughout. An embodiment in accordance with the present invention provides a centrate gate 34 internal to a centrifuge body 32. This gate is configured to allow steam sterilization of any internal passages of the gate cylinder 46 by way of a valve assembly 30.

An embodiment of the present inventive apparatus and method is illustrated generally in FIG. 1. The behavior of the centrifuge system 10 of the present invention is controlled by the system controller 12 in conjunction with various temperature sensors 18 and valves 16. This controller 12 may be a personal computer (PC), an embedded controller or a programmable logic control (PLC) preferably. The controller 12 is responsible for positioning the valves 16 and centrate gate 14 to achieve the desired actions, i.e., raising, lowering and steaming. The steaming cycle is performed in conjunction with the machine steam sterilization.

Figure 2:
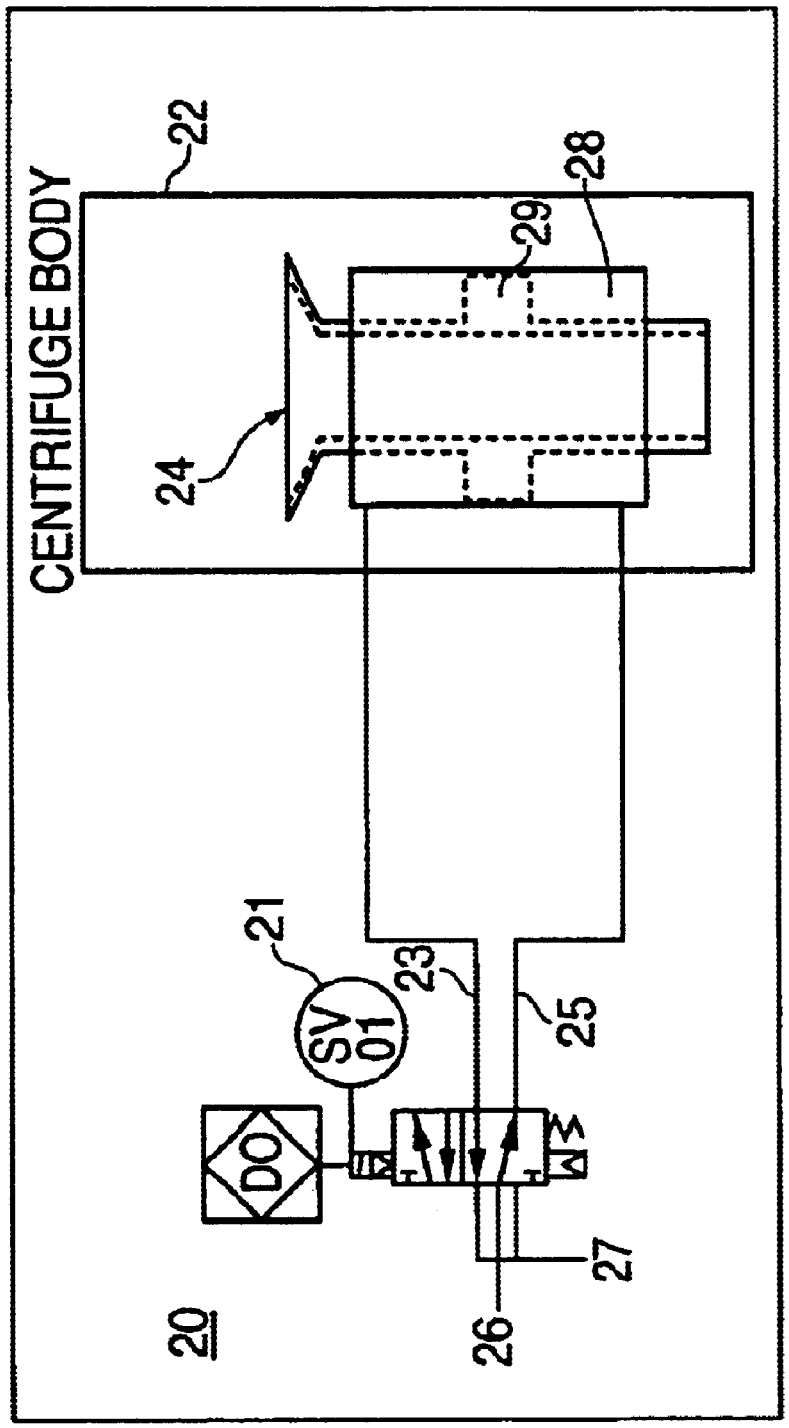
FIG. 2 is an illustration of a conventional centrate gate configuration.

Referring to FIG. 2, in a conventional centrate gate configuration 20, a valve 21 is the only control associated with the centrate gate 24, centrifuge body 22, piston 28 and cavity 29 via lines 23, 25. This valve 21 controls the air supply 26 and air exhaust 27 alone.

Figure 3:
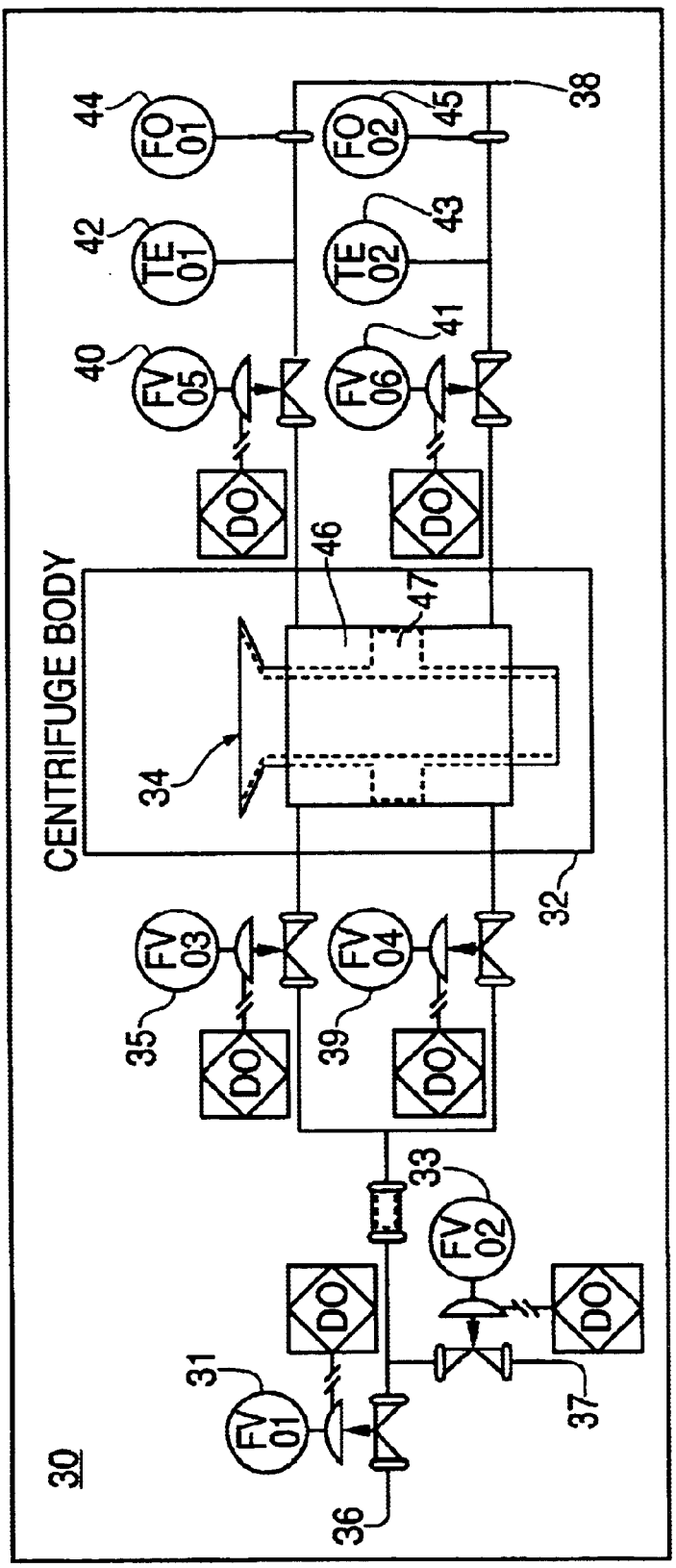
FIG. 3 is an illustration of the centrate gate and valve configuration in accordance with a preferred embodiment of the present invention.

Referring to FIGS. 1 & 3, a controller 12 determines that the system temperature has stabilized at its temperature set point Subsequently, the controller 12 then sequences the valves 16. This is done to minimize any damage to the piston seals (not shown). During the system'sat temperature hold time the controller 12 alternately raises and lowers the centrate gate 34. The controller 12 then turns the air off, vents trapped air in the piston 46, and turns the steam 37 on to allow the steam to flow through the piston cavities 47. This cycling ensures that all internal surfaces of the piston cavity 47 have direct steam contact during the cycle.

The centrate gate 34 is an internal part of a centrifuge body 32 usually in the families of industrial production and laboratory units. Its purpose is to isolate the discharged solids from the centrate discharge portion of the centrifuge body 32. This prevents the possible contamination and loss of product.

During operation, it is possible to drag liquid and possibly solid particles into the centrate gate cylinder chambers/cavities 47. If the internal chambers 47 of the gate 34 are not sterilized between product runs, it may be possible to contaminate the next batch with material from the previous batch.

As depicted in FIG. 3, a preferred embodiment of the invention provides a valve assembly 30 comprising a first control valve 35, a second control valve 39, a third control valve 40 and a fourth control valve 41. These four control valves 35, 39, 40, 41 are used together to control the gate position. The valve assembly 30 is used to allow either steam 37 or air 36 to flow through the control valves 35, 39, 40, 41 to the centrate gate 34. This invention may also require the centrate gate cylinder 46 to be double ported on both ends and either steam traps or flow orifices connected in series with the valves used to exhaust the piston cavities 47.

Again referring to FIG. 3, in the present invention, the centrate gate 34 is still controlled but it is now possible to steam sterilize the internal passages 47 of the gate cylinder 46. Positioning control is realized by using valves, 31, 35 and 41 for the raised position and valves 31, 39 and 40 to move the gate to a lowered position. Valve 31 is an air control valve.

Steaming is accomplished by closing the air control valve 31 and opening valves 35, 39, 40 and 41. This allows steam 37 to flow through the cylinder cavities 47 and out the flow or pressure orifices 44, 45. These orifices 44, 45 are sized so that there is enough pressure maintained in the gate cavities 47 to reach the desired sterilization temperature. The orifices 44, 45 are in communication with an air/condensate exhaust 38. The temperature elements 42, 43 are disposed inline with and between valves 40 and 41 and there respective orifices 44, 45 accordingly. These temperature elements 42, 43 may be preferably either resistance temperature detectors (RTD) or thermocouples. The temperature elements 42, 43 are used to detect when the temperature of the steam exiting the gate chambers 47 has reached the predetermined sterilization temperatures as desired.

The first step in sterilization is to lower the centrate gate 34. Next the air 36 to the gate cylinder 46 is turned off and valves 35, 39, 40 and 41 are opened. After a predetermined time delay the steam control valve 33 is turned on as is the steam 37 for the centrifuge body 32. When the centrifuge body 32 reaches the predetermined sterilization temperature or set point temperature and the temperature elements 42, 43 are at the sterilization temperature as well, the centrate gate's position is toggled from a lowered position to a raised position. For the duration of the steaming cycle, the centrate gate's position is toggled up and down about every 30 seconds. This process exposes all internal surfaces to live steam and minimizes cold spots in the gate 34.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of sterilizing a centrifuge, comprising the steps of:

lowering a centrate gate;

closing an air control valve in communication with a gate cylinder, opening a first control valve, a second control valve, a third control valve and a fourth control valve which are all in communication with the gate cylinder;

opening a steam control valve which is in communication with the gate cylinder thereby allowing steam to enter a piston cylinder cavity disposed within said gate cylinder;

determining a system temperature;

comparing said system temperature to a predetermined temperature; and toggling the centrate gate from a raised position to a lowered position until said predetermined temperature is reached.

2. The method of claim 1, wherein the step of closing an air control valve further comprises the step of venting trapped air within the piston cavity.

3. The method of claim 2, wherein the venting step further comprises a first orifice and a second orifice in communication with said third control valve and said fourth control valve, respectively.

4. The method of claim 3, wherein said determining a system temperature step further comprises a first temperature element and a second temperature element disposed downstream said third control valve and said fourth control valve, respectively.

5. The method of claim 4, wherein said comparing said system temperature step further comprises a controller in communication with said first temperature element and said second temperature element.

6. The method of claim 5, wherein said comparing step further comprises closing said steam control valve upon reaching said predetermined temperature.

7. The method of claim 1, wherein said toggling step comprises closing said air control valve, said first control valve and said fourth control valve in order to raise said centrate gate.

8. The method of claim 1, wherein said toggling step comprises opening said air control valve, said second control valve and said third control valve in order to lower said centrate gate.

9. An equipment sterilization apparatus, comprising:

means for lowering a centrate gate;

means for closing an air control valve in communication with a gate cylinder;

means for opening a first control valve, a second control valve, a third control valve and a fourth control valve which are all in communication with the gate cylinder;

means for opening a steam control valve which is in communication with the gate cylinder thereby allowing steam to enter a piston cylinder cavity disposed within said gate cylinder;

means for determining a system temperature;

means for comparing said system temperature to a predetermined temperature; and means for toggling the centrate gate from a raised position to a lowered position until said predetermined temperature is reached.

10. The apparatus of claim 9, wherein means for closing an air control valve further comprises means for venting trapped air within the piston cavity.

11. The apparatus of claim 10, wherein the means for venting comprises a first orifice and a second orifice in communication with said third control valve and said fourth control valve, respectively.

12. The apparatus of claim 11, wherein said means for determining a system temperature comprises a first temperature element and a second temperature element disposed downstream said third control valve and said fourth control valve, respectively.

13. The apparatus of claim 12, wherein said means for comparing said system temperature comprises a controller in communication with said first temperature element and said second temperature element.

14. The apparatus of claim 10, wherein said means for toggling comprises closing said air control valve, said first control valve and said fourth control valve in order to raise said centrate gate.

15. The apparatus of claim 10, wherein said means for toggling comprises opening said air control valve, said second control valve and said third control valve in order to lower said centrate gate.

16. A centrifuge sterilization apparatus, comprising:

a controller proximal a centrifuge body;

a centrate gate disposed within the centrifuge body;

a valve assembly in communication with the centrate gate, an air supply and a steam supply; and a plurality of temperature elements in communication with said controller, wherein said controller is configured to operate the valve assembly.

17. The apparatus of claim 16, wherein said valve assembly comprises:

a first control valve;

a second control valve;

a third control valve;

a fourth control valve;

a first pressure orifice; and a second pressure orifice.

18. The apparatus of claim 17, wherein said plurality of temperature elements comprises a first temperature element and a second temperature element disposed downstream said third and said fourth control valves, respectively.

19. The apparatus of claim 18, wherein said first pressure orifice and said second pressure orifice are disposed downstream said first temperature element and said second temperature element, respectively.

20. The apparatus of claim 16, wherein said plurality of temperature elements are temperature sensors.

* * * * *